Aug. 16, 1938. E. TOWILL Plant Pat. 282
ROSE
Filed Nov. 22, 1937
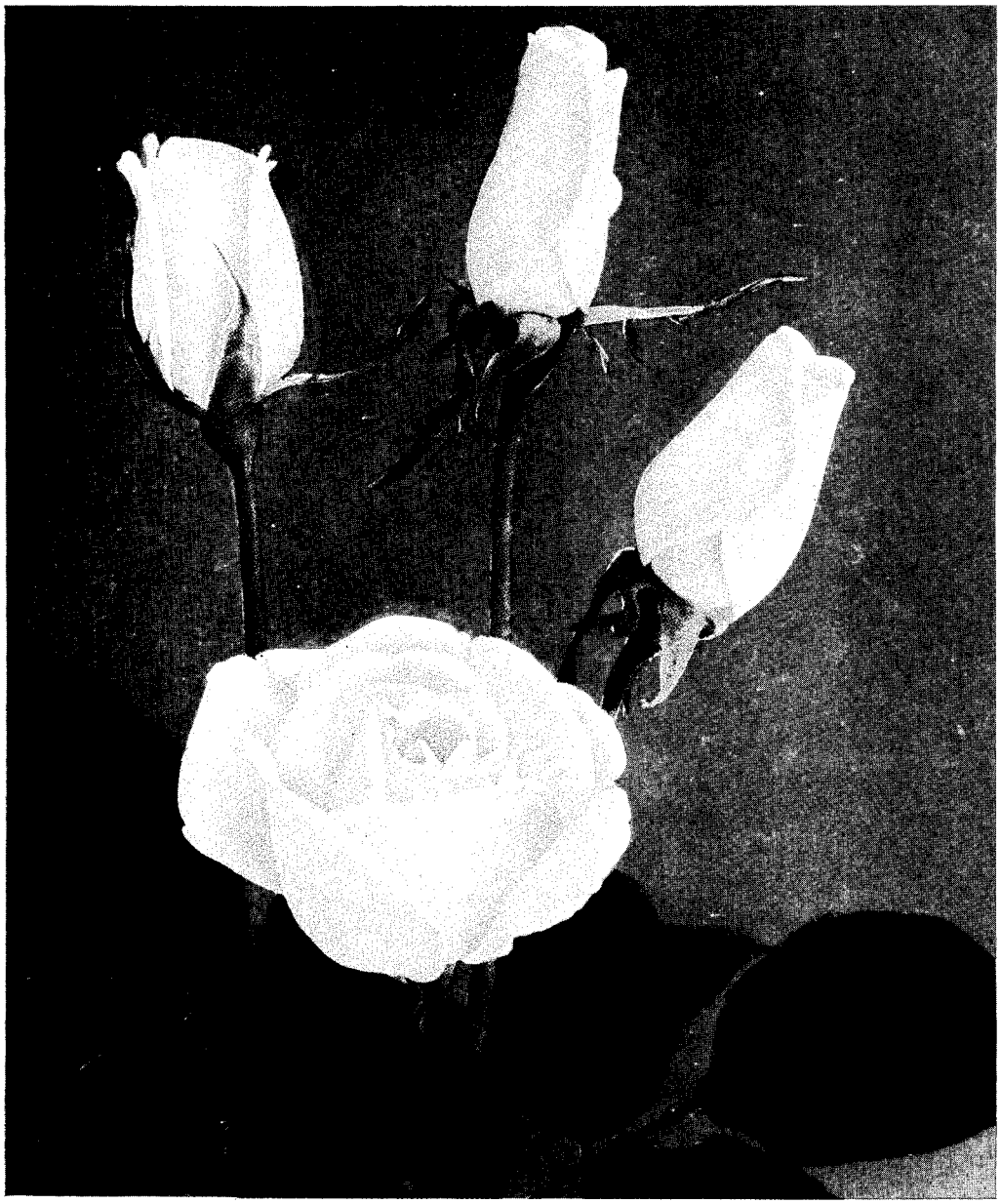
INVENTOR
Edward Towill
By Orville M. Kile
Plant Patent Agent Patented Aug. 16, 1938

Plant Pat. 282

UNITED STATES PATENT OFFICE

282

ROSE

Edward Towill, Roslyn, Pa.

Application November 22, 1937, Serial No. 175,906

1 Claim. (Cl. 47—61)

My present invention relates to improvements in roses of the Hybrid Tea class and in the yellow to orange color range. It originated as a cross between Souvenir de Claudius Pernet and an unnamed seedling which in turn was a cross between Lady Hillingdon and Harry Kirk. The final cross was made several years ago and I have since developed asexually and reproduced the present variety and proved the permanence and worth of its characteristics.

The accompanying illustration shows in full color four specimens of this new rose in various stages of opening, together with a portion of the stems and leaves.

Following is a more detailed description of this rose plant, color references being to Ridgway's Color Standards and Nomenclature.

*The plant*

*Growth habits.*—Very vigorous. Bush. Prolific producer. Flowers borne singly. Continuous and profuse bloomer.

*Disease resistance.*—Very pronounced.

*Stems.*—Biscay Green (Plate XVII), covered with many large thorns.

*Thorns.*—Red or pink; downward pointing; irregularly and frequently spaced.

*Peduncle.*—Same color as stem; covered with numerous spines and small thorns.

*Foliage.*—Very abundant.

*Leaves.*—Compound, usually five leaflets; heavy and leathery.

*Color.*—Upper surface is the shade of Dark Dull Yellow Green (Plate XXXII) but has a decided glossy appearance. Under side is nearest to Light Elm Green (Plate XVII) but is slightly grayed. Frequently the under surface has a cast of a reddish tone or of Old Rose (Plate XIII).

*Leaflets.*—Oval with sharp apex; margin sharply serrated. Large center leaflet frequently is 3¾ inches long and 2⅝ inches wide. The average is about 3¼ inches by 1⅝ in.

*Stems.*—Strong; stiff; thorn-covered; medium length.

*Rachis.*—Heavy; usually bronzed or reddish; upper side grooved; under side has several small, sharp thorns.

*Stipules.*—Short but with moderately long, sharp points; moderate in width.

*The flower*

*Bud.*—Open slowly, evenly and beautifully. When bud is small, foliaceous appendages of the sepals are double the length of the bud itself. The opening bud is very long and the sepals do not keep up with it in growth so are scarcely more than half the length of the bud in its cutting stage.

*Color.*—Outer petals blend from Orange-Buff (Plate III) at the base to Mikado Orange (Plate III) at the edges. As the bud begins to open, the petals turn back slightly, revealing the inner color of the petals which is Light Orange-Yellow (Plate III). A Lemon Chrome (Plate IV) spot is found at the base of each petal.

*Size and shape.*—Very long and slender; ranges from 1½ to 2¼ inches in length.

*Bloom.*—

*Size.*—Medium, opening to an average of 4 inches across.

*Petalage.*—Semi-double. In October the number of petals averages 25.

*Petals.*—Soft; of good substance but not leathery.

*Shape.*—Outer petals nearly round—inner petals oval.

*Form.*—Opens cup shaped.

*Color.*—Same as bud. Sometimes the inner petals are striped on the outside by the same Light Orange-Yellow (Plate III) as is found on the inside of the petal. Bloom turns lighter as it ages.

*Behavior.*—Clings tenaciously.

*Longevity.*—Lasts well both on the bush and as a cut flower.

*Fragrance.*—Moderately fragrant.

*Reproductive organs*

*Stamens.*—Exceedingly large number (70 to 75); arranged about pistils.

*Filaments.*—Of uneven lengths; some yellow, some orange.

*Anthers.*—Large; yellow, edged with orange; occasionally the anthers tend to become petaloids.

*Pistils.*—Many (25 to 30).

*Styles.*—Fairly even; bunched; yellow at base, bright red at top.

*Stigma.*—Red with yellowish tip.

*Hips.*—Relatively small.

*Sepals.*—Usually two are simple; others have appendages, one of which usually is considerably foliaceous. Recurve in early stages of bud opening.

*Comparisons*

The known varieties most nearly like my new variety are the Harry Kirk and the Joanna Hill.

This new variety differs materially from the

Harry Kirk in its color, the new one being very much more vivid. It also differs in that the new variety is borne singly whereas the Harry Kirk is borne several together on a stem. Also the stems of the new variety are a great deal stiffer and stronger, the bud is more pointed, and the plant is a much better producer.

An important difference between the new variety and the Joanna Hill is the vivid and distinctive coloring of the new variety. Also the new variety is much more vigorous and much more profuse in its blooming. It makes a better garden plant and is more resistant to disease especially blackspot. The new variety is heavily beset with thorns and splines while Joanna Hill has few thorns.

Having thus disclosed invention, what I claim is:

A new and distinct variety of rose plant as herein shown and described, characterized particularly by its blossoms of distinctive color and pleasing form, its exceptionally long pointed buds, its vigorous growth and stiff stems, and its prolific production as compared with Joanna Hill and Harry Kirk.

EDWARD TOWILL.